(12) United States Patent
Puig Serrano

(10) Patent No.: US 8,119,834 B2
(45) Date of Patent: Feb. 21, 2012

(54) PROCESS FOR THE PREPARATION OF ADAPALENE AND RELATED COMPOUNDS

(75) Inventor: Jordi Puig Serrano, Girona (ES)

(73) Assignee: Medichem, S.A., Barcelona (ES)

( * ) Notice: Subject to any disclaimer, the term of this patent is extended or adjusted under 35 U.S.C. 154(b) by 748 days.

(21) Appl. No.: 11/922,353

(22) PCT Filed: Jun. 16, 2006

(86) PCT No.: PCT/IB2006/003987
§ 371 (c)(1),
(2), (4) Date: May 1, 2008

(87) PCT Pub. No.: WO2007/072217
PCT Pub. Date: Jun. 28, 2007

(65) Prior Publication Data
US 2009/0131713 A1 May 21, 2009

Related U.S. Application Data

(60) Provisional application No. 60/691,259, filed on Jun. 17, 2005.

(51) Int. Cl.
*C07C 63/34* (2006.01)
(52) U.S. Cl. ...................................................... 562/467
(58) Field of Classification Search .................... None
See application file for complete search history.

(56) References Cited

U.S. PATENT DOCUMENTS 4,717,720 A * 1/1988 Shroot et al. .................... 514/63

FOREIGN PATENT DOCUMENTS

WO    WO 03075908 A    9/2003
WO    WO 2006108717 A    10/2006

OTHER PUBLICATIONS

Silverman, Handbook of Grignard Reagents, 1996, Marcel Dekker, New York, p. 89.*
International Search Report dated Aug. 10, 2007 for International Patent Application No. PCT/IB2006/003987.
Charpentier, Bruno et al., "Synthesis, Structure-Affinity Relationships, and Biological Activities of Ligands Binding to Retinoic Acid Receptor Subtypes" Journal of Medicinal Chemistry, 38 (26), 4993-5006 CODEN: JMCMAR; ISSN: 0022-2623, 1995 XP000971461, p. 5001, col. 2, lines 17-48.
Brenna, Elisabetta et al., "Isolation and Characterization of Impurities in Adapalene" Journal of Pharmaceutical and Biomedical Analysis, 43 (3), 1161-1163 CODEN: JPBADA; ISSN: 0731-7085, 2007, XP005870927, compounds 1, 3, paragraph [2.3.2.].
Liu, Zhichang, et al., A High Yield and Pilot Scale Process for the Preparation of Adapalene, Organic Process Research & Development, 2006, pp. 285-288, vol. 10.

* cited by examiner

*Primary Examiner* — Paul A Zucker
(74) *Attorney, Agent, or Firm* — Tristan A. Fuierer; Moore & Van Allen, PLLC

(57) ABSTRACT

The invention provides an improved process for the preparation of a benzonaphthalene derivative including, in particular, the manufacture of high purity adapalene. The invention further includes a method for assessing the color of adapalene by means of a quantitative colorimetric measurement of the produced adapalene.

4 Claims, 1 Drawing Sheet

PROCESS FOR THE PREPARATION OF ADAPALENE AND RELATED COMPOUNDS

CROSS REFERENCE TO RELATED APPLICATIONS

This application claims priority under 35 U.S.C. §371 to International Application No. PCT/IB2006/003987 (filed Jun. 16, 2006), which claims priority to U.S. Provisional Application No. 60/691,259 (filed Jun. 17, 2005), each of which applications is expressly incorporated herein by reference in its entirety.

BACKGROUND OF THE INVENTION

1. Field of the Invention

The invention provides an improved process for the preparation of a benzonaphthalene derivative. More particularly, the invention provides an improved process for the manufacture of high purity adapalene. The invention further includes a method for assessing the color of adapalene by means of a quantitative calorimetric measurement of the solid adapalene.

2. Relevant Background

The chemical name for adapalene is 6-[3-(1-adamantyl)-4-methoxyphenyl]-2-naphthoic acid, which is represented by Compound I (below):

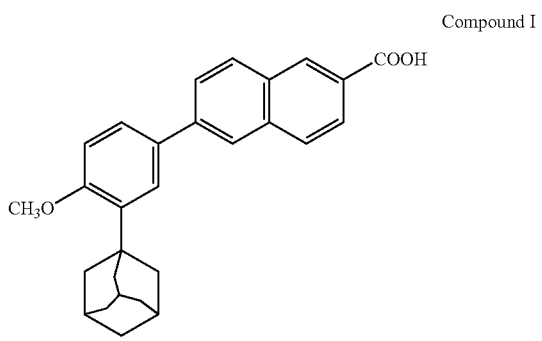

Compound I

Adapalene has been approved by the FDA as a cream, a gel, a solution and pledgets for the topical treatment of acne vulgaris and is marketed under the tradename of DIFFERIN®.

U.S. Pat. No. 4,717,720 ("the '720 patent") discloses benzonaphthalene derivatives, including adapalene. The '720 patent describes a process for preparing adapalene (i.e., according to example 9c followed by example 10) that involves two reaction steps.

The first step for preparing adapalene according to the '720 patent involves the preparation of the methyl ester of 6-[3-(1-adamantyl)-4-methoxyphenyl]-2-naphthoic acid. According to example 9c of the '720 patent, 2-(1-adamantyl)-4-bromoanisole (also known as 1-(5-bromo-2-methoxyphenyl) adamantane) is converted to its organomagnesium derivative and then into its organozinc derivative. The organozinc derivative is next coupled to methyl 6-bromo-2-naphthoate by adding a catalytic amount of $NiCl_2$/DPPE complex (also known as [bis(diphenylphosphino) ethane]dichloronickel (II)). Upon completion of the reaction, the mixture is poured into water, extracted with dichloromethane, and then dried. The product is next isolated by column chromatography by eluting with a mixture of heptane (70%) and dichloromethane (30%). The resulting product is then recrystallized in ethyl acetate (yield: 78%).

The second step for preparing adapalene according to the '720 patent involves hydrolyzing the product of step 1 (above). According to example 10 of the '720 patent, the ester obtained in Example 9c can be treated with a solution of soda in methanol followed by heating at reflux for 48 hours. The solvents are then evaporated and the resulting residue is taken up in water and acidified with concentrated HCl to neutralize the resulting adapalene sodium salt. The resulting solid is next filtered and dried under vacuum over phosphoric anhydride and then recrystallized in a mixture of tetrahydrofuran and ethyl acetate to yield adapalene (yield: 81%).

The process of preparing adapalene according to the '720 patent is both difficult and uneconomical to conduct on an industrial scale. Regarding step 1, the use of dichloromethane is both toxic and hazardous for the environment. Additionally, purification of the intermediate product by column chromatography, followed by recrystallization, in order to obtain a crystalline product of acceptable purity is both expensive and laborious. Moreover, the step 1 process produces as a biaryllic C—C bond, and the catalytic coupling is noticeably exothermic. Regarding step 2, the synthesis of adapalene and/or its sodium salt requires a long reaction time (i.e., 48 hours) at methanol reflux and further requires a high ratio of solvent (volume) to product (mass).

Additionally, according to the prior art, the manufacture of adapalene is not satisfactory for industrial implementation because the presence of high amounts of undesired by-products makes it necessary to use uneconomical purification procedures to isolate the product according to quality specifications. One significant undesired by-product produced during the Grignard reaction of step 1 in the synthesis of adapalene is 3,3'-diadamantyl-4,4'-dimethoxybiphenyl, which has not been previously described in the literature and which is represented by Compound VI (below):

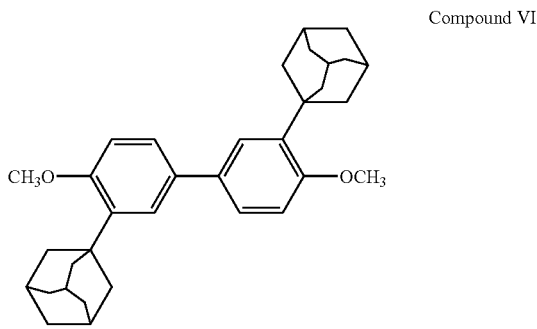

Compound VI

The level of the by-product in a sample of adapalene, adapalene methyl ester and/or an adapalene salt can be determined using standard analytical techniques known to those of ordinary skill in the art. For example, the level can be determined by HPLC. A specific method for determining the level of this impurity is provided herein.

Since the solubility of the dimeric by-product is very low in most solvents, the design of an economical industrial process that yields pure adapalene without the use of expensive chromatographic methods requires the selection of the proper solvents and conditions to inhibit formation of the by-product during the manufacturing process.

Additionally, adapalene has been described as being white (see, e.g., Merck Index, $13^{th}$ ed., p. 29). It has been observed that adapalene has a tendency to yellow under certain synthetic conditions or due to the quality of the starting materials used in its preparation. In this regard, color must be attributed to the presence of some specific impurities that may or may not be detectable by conventional methods such as HPLC.

SUMMARY OF THE INVENTION

The invention provides an improved process for the preparation of a benzonaphthalene derivative. More particularly, the invention provides an improved process for the manufacture of high purity adapalene. The invention further includes a method for assessing the color of adapalene by means of a quantitative calorimetric measurement of the solid adapalene.

Another aspect of the invention includes a method for assessing the purity of adapalene by means of a quantitative calorimetric measurement of the solid adapalene. This method consists in using a calorimeter or spectrophotometer apparatus to measure the L*, a* and b* coordinates of the solid sample of adapalene. Thus, the color of the solid sample is located in the CIE 1976 L*, a*, b* Color Space (CIELAB; CIE stands for Commission Internationale de l'Eclairage or International Commission on Illumination). The three parameters in the model represent the lightness of the color (i.e., L*, an L*=0 indicates black and an L*=100 indicates white), its position between magenta and green (i.e., a*, negative values indicate green while positive values indicate magenta) and its position between yellow and blue (i.e., b*, negative values indicate blue and positive values indicate yellow).

Thus, the process of preparing adapalene according to the invention provides adapalene that is white by visual inspection and this fact is corroborated by the colorimetric measurements that yield values in the CIELAB color space that are very close to the values of absolute white that are L*=100; a*=0; b*=0, See, e.g., US Pharmacopoeia 29$^{th}$ ed., General Chapter 1061, p. 2896.

BRIEF DESCRIPTION OF THE DRAWING

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE PREFERRED EMBODIMENTS

Figure 1:
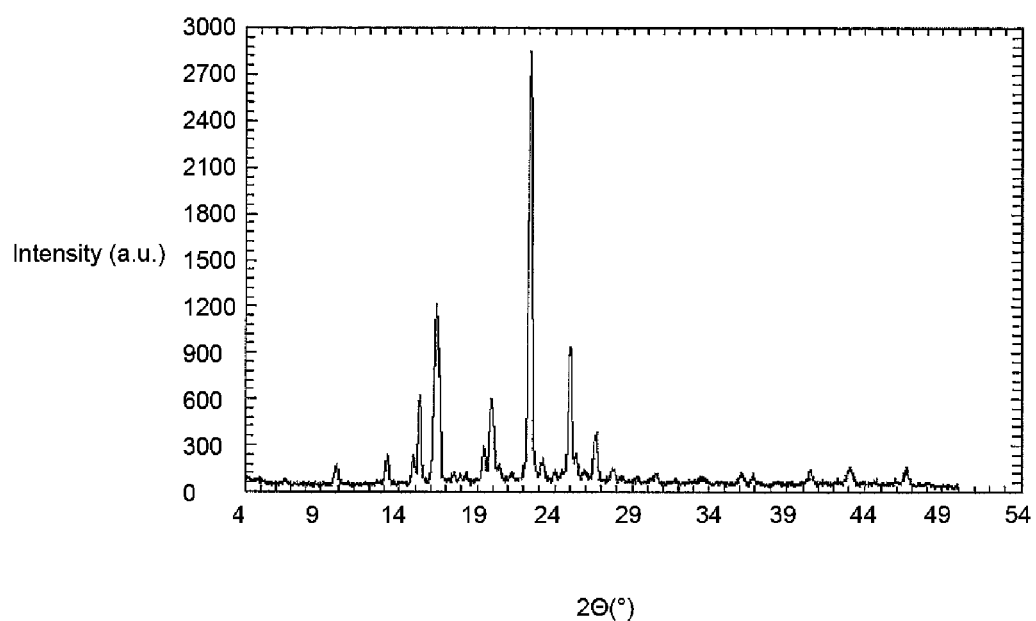
FIG. 1 illustrates the X-ray diffractogram of adapalene made in by the process of the invention.

Reference will now be made in detail to the preferred embodiments of the invention. This invention may, however, be embodied in many different forms and should not be construed as limited to the embodiments set forth herein. In addition and as will be appreciated by one of skill in the art, the invention may be embodied as a method, system or process.

The invention provides an improved process for preparing adapalene. In particular, the invention provides an improved process for preparing adapalene that includes isolating adapalene potassium salt. As illustrated in Scheme 1 (below), the process of the invention includes three reaction steps.

The first step ("step 1") of the process of the invention involves the preparation of the adapalene methyl ester as described in detail below in Example/Step 1. According to the process of the invention, step 1 includes charging the catalyst (NiCl$_2$/DPPE complex) prior to the addition of methyl 6-bromo-2-naphthoate. Doing so provides better control of the reaction and thus helps minimize the generation of heat. In particular, addition of the methyl 6-bromo-2-naphthoate over a suspension of the organozinc derivative and the catalyst minimizes the exothermic reaction and associated risks at the industrial scale.

Additionally, step 1 of the process of the invention is considerably less laborious that known procedures. In particular, the product is isolated by filtration as a solid from the reaction mixture, thus avoiding the use of dichloromethane (which also results in extraction of impurities). Once isolated, the solid product can be purified by suspending/recrystallizing it in an organic solvent (e.g., an aromatic hydrocarbon solvent, a ketone solvent, an ether solvent, an alcohol solvent, an ester solvent, water and/or mixtures thereof) therefore avoiding the need to purify the product by column chromatography. Preferable solvents include methyl ethyl ketone and/or mixtures of tetrahydrofuran and water.

The second step ("step 2") of the process of the invention involves the hydrolysis of the adapalene methyl ester to yield adapalene potassium salt. According to the process of the invention, step 2 includes performing the hydrolysis in the presence of a phase transfer catalyst in an aromatic apolar solvent (e.g., toluene). Performing the hydrolysis under these conditions reduces the reaction time from 48 hours to approximately 2 to 3 hours. Additionally, the adapalene potassium salt prepared in step 2 can be recovered from the reaction mixture by filtration. Importantly, the homocoupling product (i.e., 3,3'-diadamantyl-4,4'-dimethoxy biphenyl, Compound VI) is more soluble in aromatic apolar solvents (e.g., toluene) than the corresponding potassium salt. Thus, elimination of most, if not all, of the by-product is achieved via filtration. The adapalene potassium salt can optionally be purified by suspending/recrystallizing it in an organic solvent (e.g., an aromatic solvent, an ether solvent, a mixture of an alcohol and water and/or mixtures thereof).

It is believed that step 2 of the process of the invention can be performed using other adapalene salts other than the potassium salt. Such additional adapalene salts include, for example, the sodium salt, the lithium salt, the cesium salt and/or other salts arising from other bases that could alternatively be used for hydrolyzing the adapalene methyl ester.

The third step ("step 3") of the process of the invention involves the neutralization of the adapalene potassium salt to yield adapalene. According to the process of the invention, step 3 includes performing the neutralization in an alcoholic solvent, which facilitates the neutralization and avoids solid-solid occlusions. Additionally, the neutralization is performed at a temperature not exceeding than 40° C. in order to prevent the unwanted esterification of the adapalene product.

In step 3 of the process of the invention, insolubles can optionally be removed by filtration and decolorizing agents can optionally be employed to improve the color of the crude adapalene. Such steps can be performed in, for example, tetrahydrofuran and/or mixtures of tetrahydrofuran and water. Suitable decolorizing agents can be any conventional decolorizing agent, including, for example, alumina, activated alumina, silica, a metabisulphite salt and charcoal. The preferred decolorizing agent is a sulfur based reducing agent including, for example, metabisulphite or dithionite salts. Partial distillation of the tetrahydrofuran and, optionally, addition of a protic solvent (e.g., methanol or water) yields the desired crystalline product.

Scheme 1 illustrates the preparation of adapalene prepared according to one aspect of the invention.

Scheme 1

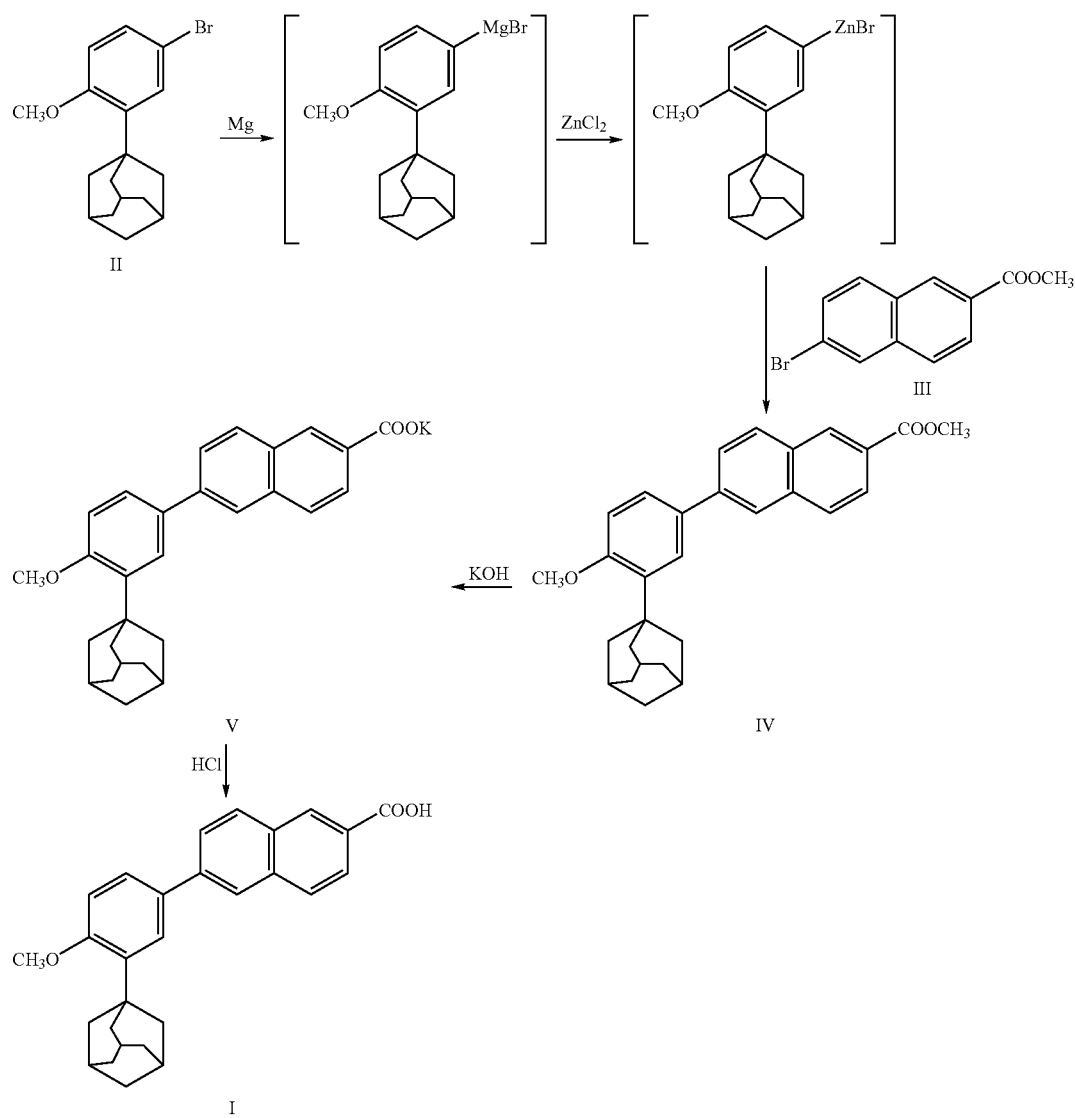

Scheme 1 legend:

| Compound | Name |
|---|---|
| I | Adapalene |
| II | 1-(5-Bromo-2-Methoxyphenyl)Adamantane |
| III | 6-Bromo-2-Naphthoate |
| IV | Methyl 6-[3-(1-adamantyl)-4-Methoxyphenyl]-2-Naphthoate |
| V | 6-[3-(1-Adamantyl)-4-Methoxyphenyl]-2-Naphthoic Acid Potassium Salt |

One aspect of the invention includes a process for preparing adapalene from a corresponding salt.

Another aspect of the invention includes a process for preparing adapalene methyl ester.

Another aspect of the invention includes adapalene salts and a process for preparing them.

Another aspect of the invention includes purifying/crystallizing adapalene salts.

Another aspect of the invention includes a process for preparing adapalene from its corresponding potassium salt.

Another aspect of the invention includes the 3,3'-diadamantyl-4,4'-dimethoxybiphenyl by-product (Compound VI, above) and its use as a reference marker for the assessment of the quality of adapalene and/or pharmaceutical compositions containing adapalene.

Another aspect of the invention includes the use of 3,3'-diadamantyl-4,4'-dimethoxybiphenyl by-product (Compound VI, above) as a reference marker for evaluating the quality of an adapalene methyl ester intermediate.

Another aspect of the invention includes the use of 3,3'-diadamantyl-4,4'-dimethoxybiphenyl by-product (Compound VI, above) as a reference marker for measuring the quality of an adapalene salt intermediate.

Another aspect of the invention includes charging the NiCl$_2$/DPPE complex before the addition of methyl 6-bromo-2-naphthoate in the catalytic coupling step.

Another aspect of the invention includes washing adapalene methyl ester with a solvent that includes an aromatic hydrocarbon solvent, a ketone solvent, an ether solvent, an alcohol solvent, an ester solvent, water and/or mixtures thereof, thus avoiding the need to purify the product by column chromatography. Preferable solvents include methyl ethyl ketone and/or mixtures of tetrahydrofuran and water.

Another aspect of the invention includes using a phase transfer catalyst and a base to hydrolyze adapalene methyl ester.

Another aspect of the invention includes using a phase transfer catalyst and an inorganic base to hydrolyze adapalene methyl ester.

Another aspect of the invention includes using a phase transfer catalyst and an inorganic base, preferably an alkali hydroxide, to hydrolyze adapalene methyl ester.

Another aspect of the invention includes using a phase transfer catalyst and an inorganic base, preferably an alkali hydroxide, and most preferably potassium hydroxide, to hydrolyze adapalene methyl ester.

Another aspect of the invention includes using a phase transfer catalyst to hydrolyze adapalene methyl ester, where the phase transfer catalyst is a quaternary ammonium salt.

Another aspect of the invention includes using a phase transfer catalyst to hydrolyze adapalene methyl ester, where the phase transfer catalyst is a quaternary ammonium salt, preferably a tetraalkylammonium halide and, most preferably, tetrabutylammonium bromide.

Another aspect of the invention includes using an apolar solvent, preferably an aromatic apolar solvent, and most preferably toluene to hydrolyze adapalene methyl ester.

Another aspect of the invention includes using a reaction time of less than approximately 3 hours to hydrolyze adapalene methyl ester.

Another aspect of the invention includes washing an adapalene salt with a solvent, including, for example, an aromatic hydrocarbon, esters, ethers, ketones, alcohols and water or a mixture thereof, and, preferably, mixtures of tetrahydrofuran and toluene and/or mixtures of methanol and water.

Another aspect of the invention includes using adapalene methyl ester that contains variable amounts of dimeric compound of Compound VI when hydrolyzing adapalene methyl ester.

Another aspect of the invention includes purifying adapalene by decolorizing and/or filtering a dissolution of adapalene.

Another aspect of the invention includes using methanol when neutralizing an adapalene salt.

Another aspect of the invention includes removing by filtration any insoluble particles of a solution of adapalene in tetrahydrofuran.

Another aspect of the invention includes decolorizing adapalene in tetrahydrofuran and, preferably, using a decolorizing agent that is a salt of metabisulphite and, more preferably, sodium metabisulphite.

Another aspect of the invention includes a partial distillation of tetrahydrofuran and filtration of the precipitated adapalene.

Another aspect of the invention includes a partial distillation of tetrahydrofuran and precipitation of adapalene that includes adding a protic solvent, preferably methanol or water.

Another aspect of the invention includes a process for preparing adapalene of high purity.

Another aspect of the invention includes a process for preparing adapalene of high purity and, preferably, where the adapalene is more than 99.8% pure when analyzed according to reverse phase high performance liquid chromatography and, more preferably, more than 99.9% pure when analyzed by reverse phase high performance liquid chromatography.

Another aspect of the invention includes a process for preparing adapalene of high purity where the adapalene is 100.0% pure when analyzed according to reverse phase high performance liquid chromatography.

Another aspect of the invention includes a process for preparing adapalene having a residue on ignition of less than 0.1% and, more preferably, less than 0.05%.

Another aspect of the invention includes using adapalene of high purity in the manufacture of pharmaceutical compositions.

Another aspect of the invention includes adapalene that is substantially white by visual inspection.

Another aspect of the invention includes substantially white adapalene having the following measurements in the CIE (1976) L*, a*, b* Color Space (CIELAB) when using a calorimeter or spectrophotometer, illuminant D65 (daylight) and a 2° angle of observation:

| | |
|---|---|
| L* | 98.5 to 100 |
| a* | −0.38 to −0.60 |
| b* | +0.31 to +0.93 |

Another aspect of the invention includes substantially white adapalene having the following measurements in the CIE (1976) L*, a*, b* Color Space (CIELAB) when using a colorimeter or spectrophotometer, illuminant C and a 2° angle of observation:

| | |
|---|---|
| L* | 97.30 to 98.47 |
| a* | +0.20 to +0.45 |
| b* | 0.00 to −0.75 |

Another aspect of the invention includes a method for assessing the purity of adapalene by means of a quantitative calorimetric measurement of the solid adapalene. In this method, the L*, a* and b* coordinates of a solid sample of adapalene are measured using a calorimeter or spectrophotometer apparatus.

It will be apparent to those skilled in the art that various modifications and variations can be made in the present invention and specific examples provided herein without departing from the spirit or scope of the invention. Thus, it is intended that the present invention covers the modifications and variations of this invention that come within the scope of any claims and their equivalents.

SPECIFIC EXAMPLES

The following examples are for illustrative purposes only and are not intended, nor should they be interpreted to, limit the scope of the invention.

Example

Step 1: Preparation of Methyl 6-[3-(1-adamantyl)-4-methoxy phenyl]-2-naphthoate (i.e., Adapalene Methyl Ester)

To a 2 L, five-necked cylindrical reaction vessel equipped with a reflux condenser, heat-transfer jacket, compensated-pressure addition funnel, anchor impeller and purged with nitrogen, were added 1.13 g of 1-(5-bromo-2-methoxyphenyl)adamantane ($3.52 \times 10^{-3}$ mol), 3.75 g of magnesium granules ($1.54 \times 10^{-1}$ mol) and 90 mL of tetrahydrofuran. Into the compensated-pressure addition funnel was added a previously prepared solution of 36.37 g of 1-(5-bromo-2-methoxyphenyl)adamantane ($1.13 \times 10^{-1}$ mol) and 270 mL of tetrahydrofuran. The reaction mixture was then heated to approximately 45° C., at which point 2.50 g of 1,2-dibromoethane ($1.33 \times 10^{-2}$ mol) was charged to the mixture. During the addition, the internal temperature increased and bubbling was observed, indicating initiation of the reaction.

At approximately 50° C., addition of the solution in the compensated-pressure addition funnel was initiated and continued over approximately 45 minutes during which time the internal temperature of the solution was maintained between approximately 50 and 55° C. Following the addition, the reaction mixture was stirred for approximately 45 minutes at approximately 50° C. and then cooled to approximately 20-25° C. To the cooled suspension was added 18.18 g of anhydrous zinc chloride ($1.33 \times 10^{-1}$ mol) and an increase in temperature was observed within a few seconds. The mixture was permitted to cool and was stirred for approximately 1 hour at approximately 20-25° C. Thereafter, 1.05 g of 1,2-[bis(diphenylphosphino)ethane]dichloronickel(II) ($2.20 \times 10^{-3}$ mol) was charged to the reaction mixture followed by the addition of 24.00 g of methyl 6-bromo-2-naphthoate ($9.05 \times 10^{-2}$ mol). The mixture was permitted cool and was stirred for approximately two hours at room temperature.

Next, 50 mL of water was slowly added and the mixture was stirred for approximately 15 minutes, at which point 200 mL of 1N HCl was slowly added. The mixture was then stirred overnight at room temperature or until the excess of magnesium pellets were dissolved. The mixture was then filtered, and the cake was washed with methyl ethyl ketone ("MEK"). The resulting solid was next suspended in 500 mL of 1N HCl and 125 mL of MEK. The resulting suspension was then stirred at room temperature for approximately 1 hour. The mixture was then filtered, and the cake was washed with MEK. The resulting solid was next suspended in 270 mL of MEK and the mixture was heated to reflux for approximately 30 minutes, cooled and filtered. The resulting cake was then washed with MEK.

The wet solid obtained was suspended in 184 mL of tetrahydrofuran and was heated to approximately 50-60° C. for approximately 30 minutes, cooled and precipitated by addition of 300 mL of methanol. The precipitate was then filtered and dried at approximately 60° C. in a vacuum oven to yield 34.31 g of adapalene methyl ester ($8.044 \times 10^{-2}$ mol; yield: 88.83%) as an off-white powder. Analytical data: HPLC Purity (HPLC at 272 nm): 97.32%; Impurity (i.e., 3,3'-diadamantyl-4,4'-dimethoxybiphenyl) area percent (HPLC at 272 nm): 2.05%.

The product may also contain a small amount of an unidentified impurity, which is more polar than the final product. This unidentified impurity, when observed, as well as the 3,3'-diadamantyl-4,4'-dimethoxybiphenyl impurity, are eliminated from the synthetic pathway during the work-up described in the Example/Step 2 (below).

Example

Step 2: Preparation of 6-[3-(1-adamantyl)-4-methoxy phenyl]-2-naphthoic acid-potassium Salt (i.e., Adapalene Potassium Salt)

In a 2 L, five necked cylindrical reaction vessel equipped with reflux condenser, distillation kit, heat-transfer jacket, anchor impeller and purged with nitrogen, were added 48.38 g (dry equivalent amount) of methyl 6-[3-(1-adamantyl)-4-methoxyphenyl]-2-naphthoate ($1.134 \times 10^{-1}$ mol), wet with methanol, 2.73 g of tetrabutylammonium bromide ($8.47 \times 10^{-3}$ mol), 18.39 g of potassium hydroxide (85% alkali content, freshly titrated. $2.79 \times 10^{-1}$ mol) and 581 mL of toluene. The mixture was heated to reflux temperature, and the methanol/water was removed by distillation. The distilled mixture was replaced by pure toluene and the mixture was stirred at reflux for approximately three hours (including the time required for the distillation). The solution was then cooled to approximately 20-25° C., filtered and the resulting solid was washed with toluene.

The solid was next suspended in 187 mL of tetrahydrofuran and stirred for approximately 30 minutes. Then, 375 mL of toluene was added, and the mixture was heated to reflux and maintained at that temperature for approximately 1 hour. The solution was then cooled to approximately 20-25° C., filtered, and the resulting solid washed with toluene. The toluene-wet product was then suspended in 256 mL of methanol, heated to reflux for approximately 30 minutes and cooled to 50-60° C. After cooling, 409 mL of water was added dropwise. The mixture was then again heated to reflux for approximately 15 additional minutes, cooled to room temperature and filtered. The resulting solid was washed with water to yield 50.69 g (wet) of adapalene potassium salt ($1.12 \times 10^{-1}$ mol, dry equivalent amount calculated from loss on drying; yield: 99.18%). Analytical data: HPLC Purity (HPLC at 272 nm): 99.86%; Impurity (i.e., 3,3'-diadamantyl-4,4'-dimethoxybiphenyl) area percent (HPLC at 272 nm): not detected; $^1$H-NMR (300 MHz, CD$_3$OD): δ 1.83 (broad s, 6H), 2.08 (broad s, 3H), 2.21 (broad s, 6H), 3.88 (s, 3H), 7.04 (d, 1H, J=8.4 Hz), 7.56 (overlapped, 1H, J=2.4, 9.6 Hz), 7.57 (overlapped s, 1H), 7.74 (dd, 1H, J=8.7, 1.8 Hz), 7.87 (d, 1H, J=9.0 Hz), 7.97 (d, 1H, J=8.7 Hz), 8.00 (broad d, 1H, J=0.9 Hz), 8.06 (dd, 1H, 8.4, J=1.8 Hz), 8.47 (broad d, 1H, J=0.9 Hz); $^{13}$C-NMR (75.4 MHz, CD$_3$OD): δ 30.6, 38.3, 41.8, 55.5, 113.3, 125.3, 126.4, 126.6, 127.8, 128.3, 130.0, 130.4, 133.0, 134.2, 136.1, 136.3, 139.7, 141.1, 159.9, 175.4.

Example

Step 3: Preparation of 6-[3-(1-adamantyl)-4-methoxy phenyl]-2-naphthoic Acid (i.e., Adapalene)

In 500 mL of methanol was added 49.59 g ($1.10 \times 10^{-1}$ mol, dry equivalent amount) of the wet solid obtained in Example/Step 2, and the mixture was heated to reflux for 30 minutes and cooled to approximately 40° C. Next, 33.17 g of concentrated HCl was slowly added over approximately 1 hour with gentle stirring in order to ensure homogeneity, followed by the slow addition of 248 mL of water. The resulting mixture was stirred for approximately 30 additional minutes at approximately 40° C. and then cooled to room temperature, filtered and washed with methanol. The wet solid was then suspended with 1020 mL of tetrahydrofuran and heated to reflux for approximately 10 minutes or until complete dissolution. The solution was then cooled to approximately 35° C., the solid particles were removed by filtration, and the filter was washed with tetrahydrofuran.

The collected mother liquors were heated to reflux, and 654 g of tetrahydrofuran was removed by distillation. The mixture was then cooled to approximately 55-60° C. Thereafter, 650 mL of methanol was added over approximately 10 minutes, and the mixture heated to reflux for approximately 30 minutes, cooled, and filtered. The resulting solid was filtered with methanol and dried at 80° C. in a vacuum oven to yield 40.54 g of adapalene ($9.83 \times 10^{-2}$ mol; yield: 89.29% (from adapalene potassium salt); 88.56% (from adapalene methyl ester); and 78.67% (from methyl 6-bromo-2-naphthoate)). Analytical data: HPLC Purity (HPLC at 272 nm): 100.00%; Assay: 99.99%; Residue on Ignition: 0.02%; IR: matches reference.

Table 1 (below) lists the peak assignments of the X-ray powder diffractogram of the adapalene obtained and are illustrated in FIG. 1.

TABLE 1

| peak | peak_position | peak_intensity | background |
|---|---|---|---|
| 1 | 9.94547 | 175.32198 | 42.94638 |
| 2 | 13.18338 | 239.32156 | 48.88440 |
| 3 | 14.87487 | 234.32591 | 47.91444 |
| 4 | 15.28319 | 573.40082 | 53.73505 |
| 5 | 16.37472 | 1207.21631 | 69.64595 |
| 6 | 16.54000 | 882.00000 | 68.42529 |
| 7 | 17.39657 | 110.88804 | 58.39248 |
| 8 | 17.93203 | 114.02068 | 55.36037 |
| 9 | 19.44575 | 285.34473 | 113.52401 |
| 10 | 19.94692 | 569.60516 | 153.63921 |
| 11 | 22.43198 | 2846.14307 | 110.81189 |
| 12 | 24.02238 | 140.20882 | 85.37505 |
| 13 | 25.04586 | 925.64282 | 121.97974 |
| 14 | 25.41035 | 240.42351 | 102.81077 |
| 15 | 26.68556 | 362.45480 | 68.05973 |
| 16 | 27.71646 | 141.77916 | 72.53469 |
| 17 | 40.51307 | 133.00453 | 43.44914 |
| 18 | 46.52728 | 130.31587 | 50.16773 |

Example

Step 4: Preparation of 3,3'-diadamantyl-4,4'-dimethoxybiphenyl

To a 100 mL rounded bottom reaction vessel equipped with a magnetic stirrer, thermometer, reflux condenser, pressure compensated addition funnel, were added 0.15 g of 1-(5-bromo-2-methoxyphenyl)adamantane, 0.47 g of magnesium turnings and 7 mL of tetrahydrofuran. The mixture was heated to approximately 35° C., and 0.13 mL of 1,2-dibromoethane were added to the mixture. Reaction exothermy self-heated the mixture. Next, a solution of 4.85 g of 1-(5-bromo-2-methoxyphenyl)adamantane and 28 mL of tetrahydrofuran was added to the mixture dropwise. During this addition, the temperature of the mixture dropped from reflux temperature to approximately 45° C. The reaction was then stirred for approximately 45 additional minutes at approximately 45° C. and was permitted to cool to approximately 22° C. Next, 2.3 g of $ZnCl_2$ was added to the mixture, resulting in an exothermic reaction that raised the temperature of the mixture to approximately 38° C. The mixture was then permitted to cool to approximately 22° C. and was stirred for approximately 1 hour at this temperature.

Next, 0.03 g of $Pd(OAc)_2$ and 3.5 g of 1-(5-bromo-2-methoxyphenyl) adamantane were added to the mixture, followed by 25 mL of tetrahydrofuran in order to improve agitation, and the mixture was heated at reflux for approximately 24 hours. The resulting mixture was then evaporated to dryness and poured into 103 mL of 0.015 N HCl. Next, 150 mL of dichloromethane and 100 mL of water were added to yield a mixture consisting of a solid, an aqueous layer and an organic layer. The mixture was then filtered to separate the solid, the aqueous layer was discarded, and the organic layer was washed with 200 mL of water and decanted again. This process was repeated twice on the filtered solid. The three collected organic layers were evaporated to dryness, washed in methanol, and dried to yield 2.1 g of 3,3'-diadamantyl-4,4'-dimethoxybiphenyl (yield: 39.9%). Analytical data: Melting point: 288.1-289.1° C.; Elemental analysis: C 83.63%, H 8.73%; $^1$H-NMR (300 MHz, $CDCl_3$): δ 1.78 (broad s, 12H), 2.08 (broad s, 6H), 2.15 (broad s, 12H), 3.86 (s, 6H), 6.92 (dm, 2H, J=8.1 Hz), 7.34 (dd, 2H, J=2.4, 8.1 Hz), 7.39 (d, 2H, J=2.4 Hz); $^{13}$C-NMR (75.4 MHz, $CDCl_3$): δ 29.2, 37.1, 37.2, 40.6, 55.1, 111.9, 125.0, 125.5, 134.0, 138.5, 157.8; MS (EI, 70 eV): m/z=484 (6), 483 (36), 412 (1,100), 410 (5), 347 (8), 135 (22), 107 (7), 93 (14), 79 (17), 67 (9), 55 (6); IR (Selected absorption bands): 2992, 2964, 2898, 2850, 1603 $cm^{-1}$.

Example 5

Colorimetric Measurement

Adapalene was prepared according to the procedure described above, with the exception that the crude product was stirred twice in a mixture of THF/methanol at 20° C. instead of being refluxed in methanol (as indicated above). This change, however, is not relevant to the final product color. The results of the colorimetric measurement (according to the CIE 1976 L*, a*, b* color space) are illustrated in Tables 2 and 3.

TABLE 2

| | L* | a* | b* |
|---|---|---|---|
| Value | 99.11 | −0.52 | 0.86 |
| Standard Deviation | 0.10 | 0.02 | 0.06 |
| Number of Replicates: 7 | | | |
| Illuminant: $D_{65}$ | | | |
| Measurement geometry: 2° | | | |
| White Index (WI E313): 93.85 | | | |

The whiteness of the adapalene sample was then obtained by depositing, leveling and measuring the sample without any special compacting treatment. The results of the whiteness measurement are illustrated in Table 3. It should be noted that the lab coordinates are necessarily different for the same sample since the illuminant used is different.

TABLE 3

| | L* | a* | b* |
|---|---|---|---|
| Value | 97.97 | 0.24 | −0.02 |
| Standard Deviation | 0.07 | 0.03 | 0.01 |
| Number of Replicates: 3 | | | |
| Illuminant: C | | | |
| Measurement geometry: 2° | | | |
| White Index (WI E313): 94.35 | | | |

The White Index (WI) was calculated according to ASTM E313-05 "Standard Practice for Calculating Yellowness and Whiteness Indices from Instrumentally Measured Color Coordinates" using the following formula:

$$WI = Y + (WI, x)(x_n - x) + (WI, y)(y_n - Y)$$

Where: $x_n$ and $y_n$ are the chromaticity coordinates for the CIE Standard illuminant and source used, WI,x and WI,y are numerical coefficients, and Y, x, and y are the luminance factor and the chromaticity coordinates of the specimen (which can be derived from the L, a, b coordinates for a given illuminant and measurement geometry).

Values for all these variable (except those measured for the specimen) are provided in Table 4.

TABLE 4

| Illuminant/Measurement Geometry | $D_{65}/2°$ | $C/2°$ |
|---|---|---|
| $x_n$ | 0.3127 | 0.3101 |
| $y_n$ | 0.3290 | 0.3161 |
| WI,x | 800 | 800 |
| WI,y | 1700 | 1700 |

General Experimental Conditions:

A. Raw Materials

The 6-bromo-2-naphthoate and 1-(5-bromo-2-methoxyphenyl)adamantane test solution were prepared by adding 20 mg, accurately weighed, of the substance to be examined into a 100 mL volumetric flask. To the flask was added 5 mL of tetrahydrofuran and the solution was sonicated until the sample dissolved. Next, 60 mL of mobile phase was added, the sample was sonicated again, and the flask was filled to 100 mL with mobile phase.

B. Intermediates and Final Product Test

The methyl 6-[3-(1-adamantyl)-4-methoxyphenyl]-2-naphthoate test solution (i.e., adapalene methyl ester) was prepared by adding 20 mg, accurately weighed, of the substance to be examined into a 100 mL volumetric flask. To the flask was added 5 mL of tetrahydrofuran and the solution was sonicated until the sample dissolved. Next, 60 mL of mobile phase was added, the sample was sonicated again, and the flask was filled to 100 mL with mobile phase.

The 6-[3-(1-adamantyl)-4-methoxyphenyl]-2-naphthoic acid (i.e., adapalene) or its potassium salt test solution was prepared by adding 20 mg, accurately weighed, of the substance to be examined into a 100 mL volumetric flask. To the flask was added 5 mL of tetrahydrofuran and the solution was sonicated until the sample dissolved. Next, 60 mL of mobile phase was added, the sample was sonicated again, and the flask was filled to 100 mL with mobile phase.

C. Impurities Standard Solutions

The impurity 3,3'-diadamantyl-4,4'-dimethoxybiphenyl standard solution was prepared by dissolving 20 mg, accurately weighed, of 3,3'-diadamantyl-4,4'-dimethoxybiphenyl working standard in 100 mL of tetrahydrofuran in a volumetric flask which was diluted 1 mL to 100 mL with mobile phase.

D. Colorimetric Measurement

Colorimetric measurements were obtained using two different sets of equipment. Measurements using illuminant D65 were obtained using a Chroma meter CR-300 (Minolta brand) and a measurement geometry of 2°. Measurements using illuminant C were obtained using a Technibrite ERIC-950 (Technidyne Corporation) Spectrophotometer and a measurement geometry of 2°.

E. Chromatographic Separation

In each of the foregoing examples/steps, the chromatographic separation (i.e., HPLC analysis) was performed by reversed-phase chromatography in a Symmetry C18 column of 5 μm and 250×4.6 mm, using an isocratic system comprising a mobile phase prepared by mixing acetonitrile, tetrahydrofuran, water, trifluoroacetic acid (43:30:27:0.02 v/v/v/v). This mobile phase was mixed and filtered through a 0.22 μm filter under vacuum. The chromatograph was equipped with a 235/272 nm dual wavelength detector, and the flow rate was 1.0 mL per minute at room temperature.

Although the invention has been described and illustrated with a certain degree of particularity, it is understood that the present disclosure has been made only by way of example, and that numerous changes in the conditions and order of steps can be resorted to by those skilled in the art without departing from the spirit and scope of the invention.

What is claimed is:

1. A method for assessing the purity of at least one of adapalene, adapalene methyl ester, an adapalene salt and pharmaceutical compositions containing them comprising the steps of:
    (a) providing a standard solution of 3,3'-diadamantyl-4,4'-dimethoxybiphenyl; and
    (b) using the solution as a reference marker to determine the level of 3,3'-diadamantyl-4,4'-dimethoxybiphenyl impurity.

2. The method according to claim 1 for assessing the purity of adapalene methyl ester.

3. The method according to claim 1 for assessing the purity of at least one of adapalene and pharmaceutical compositions containing it.

4. The method according to claim 1 for assessing the purity of at least one of an adapalene salt and pharmaceutical compositions containing it.

* * * * *